US012668557B2

(12) United States Patent　　　　　　(10) Patent No.: US 12,668,557 B2
Piotrowski et al.　　　　　　　　　　　(45) Date of Patent: Jun. 30, 2026

(54) PROCESS FOR PREPARING AN OLEFIN STREAM FOR OLIGOMERIZATION WITH SELECTIVE HYDROGENATION

(71) Applicant: UOP LLC, Des Plaines, IL (US)

(72) Inventors: Andrew Piotrowski, Chicago, IL (US); Ernest J. Boehm, Hanover Park, IL (US); John J. Senetar, Naperville, IL (US); Matthew C. Cole, Evanston, IL (US); Jeannie Mee Blommel, Oregon, WI (US); Christopher Procopi, Glencoe, IL (US); Ian G. Horn, Streamwood, IL (US); Andrew B. Chin, Wilmette, IL (US)

(73) Assignee: UOP LLC, Rosemont, IL (US)

( * ) Notice: Subject to any disclaimer, the term of this patent is extended or adjusted under 35 U.S.C. 154(b) by 166 days.

(21) Appl. No.: 18/417,177

(22) Filed: Jan. 19, 2024

(65) Prior Publication Data

US 2024/0246890 A1　　　Jul. 25, 2024

Related U.S. Application Data

(60) Provisional application No. 63/480,895, filed on Jan. 20, 2023.

(51) Int. Cl.
*C07C 5/08*　　　(2006.01)
*C07C 2/06*　　　(2006.01)
*C07C 2/08*　　　(2006.01)

(52) U.S. Cl.
CPC ................. *C07C 5/08* (2013.01); *C07C 2/06* (2013.01); *C07C 2/08* (2013.01); *C07C 2523/72* (2013.01)

(58) Field of Classification Search
CPC .... C07C 5/05; C07C 5/08; C07C 5/09; C07C 2523/72; C07C 2/06; C07C 2/08; C07C 2/10; C07C 2/12; C07C 2/24
See application file for complete search history.

(56) References Cited

U.S. PATENT DOCUMENTS

| | | | | |
|---|---|---|---|---|
| 5,998,685 | A | * 12/1999 | Nierlich | ................. C07C 7/163 585/329 |
| 2010/0081854 | A1* | 4/2010 | Cross, Jr. | ................. C07C 7/10 585/331 |
| 2011/0245559 | A1* | 10/2011 | da Silva Ferreira Alves | .............. C10G 3/42 585/323 |

* cited by examiner

*Primary Examiner* — In Suk C Bullock
*Assistant Examiner* — Jason Y Chong
(74) *Attorney, Agent, or Firm* — Paschall & Associates, LLC; James C. Paschall

(57) ABSTRACT

A process for preparing an olefin stream for oligomerization comprises fractionating an olefin stream to provide a light gas stream and a olefin rich stream. The olefin rich stream is selectively hydrogenated to convert diolefins to mono-olefins and provide a mono-olefin stream and oligomerizing the mono-olefin stream over an oligomerization catalyst to provide an oligomerized stream.

20 Claims, 4 Drawing Sheets

PROCESS FOR PREPARING AN OLEFIN STREAM FOR OLIGOMERIZATION WITH SELECTIVE HYDROGENATION

FIELD

The field is the conversion of olefins to distillate. The field may particularly relate to preparing olefins for oligomerization to distillate fuels.

BACKGROUND

Molecular sieves such as microporous crystalline zeolite and non-zeolitic catalysts, particularly silicoaluminophosphates (SAPO), are known to promote the conversion of oxygenates such as methanol to light olefins. The highly efficient Methanol to Olefin (MTO) process may convert oxygenates to light olefins which had been typically considered for plastics production. Light olefins produced from the MTO process are concentrated in ethylene and propylene but includes C4-C8 olefins.

Ethylene can be oligomerized into olefins such as C4, C6 and C8 olefins. Propylene can be oligomerized into olefins such as C6, C9 and C12 olefins. Larger MTO olefins can also be oligomerized. Olefin oligomerization is a process that can oligomerize smaller olefins into larger olefins. More specifically, it can convert olefins into a distillate range carbon length molecule including jet fuel and diesel range products. The oligomerized distillate can be saturated for use as transportation fuels.

Jet fuel is one of the few petroleum fuels that cannot be replaced easily by electrical motor systems because a high energy output is required to fuel planes which cannot be supplied with electric motors. Jet fuel has an end point boiling specification of less than 300° C. using ASTM D86. Large incentives are currently available for renewable jet fuel in certain regions.

Product olefin streams from an MTO unit includes water and oxygenates that require removal before encountering the oligomerization catalyst. Additionally, the product olefin streams may include diolefins and acetylenes that can polymerize in the oligomerization reactor, foul the process and require cleaning, and significantly reduce selectivity to distillates range fuels. An efficient process is desired for preparing renewable olefinic feed streams for oligomerization to distillates range fuels.

BRIEF SUMMARY

We have formulated a process for preparing an olefin stream for oligomerization comprising fractionating an olefin stream to provide a light gas stream and a olefin rich stream. The olefin rich stream is selectively hydrogenated to convert diolefins to mono-olefins and provide a mono-olefin stream and oligomerizing the mono-olefin stream over an oligomerization catalyst to provide an oligomerized stream.

DEFINITIONS

Figure 1:
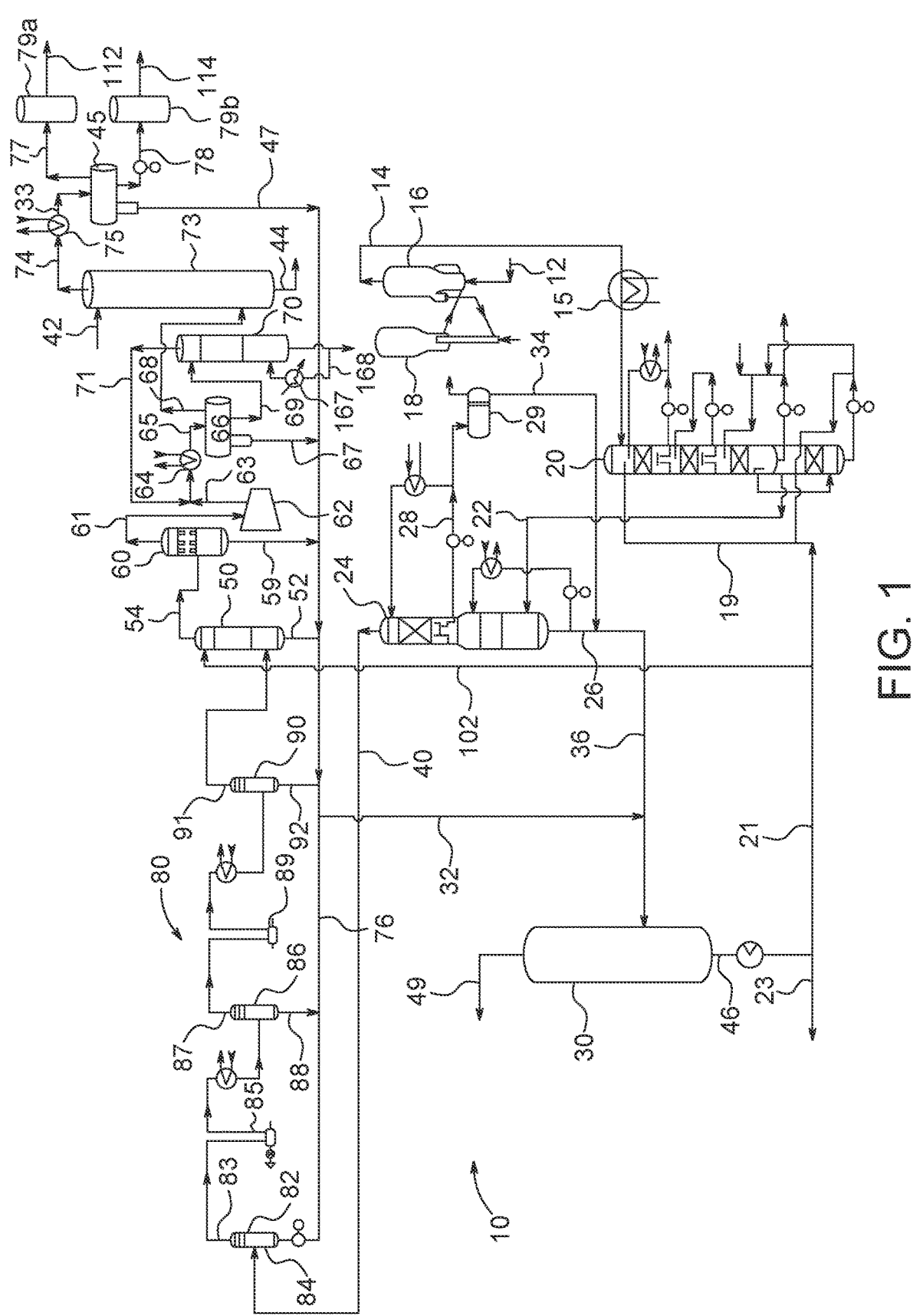
FIG. 1 is a schematic drawing of an olefinic feed preparation process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripping columns may omit a reboiler at a bottom of the column and instead provide heating requirements and separation impetus from a fluidized inert media such as steam. Stripping columns typically feed a top tray and take main product from the bottom. A column may also mean an extraction column for separating one or more components from a stream into an extract stream via liquid-liquid contact. A column may also mean an absorption column for separating one or more components from a gas stream into a liquid solvent stream.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5", "T10", "T90" or "T95" means the temperature at which 5 mass percent, 10 mass percent, 90 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "diesel" means hydrocarbons boiling in the range of an IBP between about 125° C. (257° F.) and about 175° C. (347° F.) or a T5 between about 150° C. (302° F.) and about 200° C. (392° F.) and the "diesel cut point" comprising a T95 between about 343° C. (650° F.) and about 399° C. (750° F.) using the TBP distillation method or a T90 between 280° C. (536° F.) and about 340° C. (644° F.) using ASTM D-86. The term "green diesel" or "renewable jet fuel" means diesel comprising hydrocarbons not sourced from fossil fuels.

As used herein, the term "jet fuel" means hydrocarbons boiling in the range of a T10 between about 190° C. (374° F.) and about 215° C. (419° F.) and an end point of between about 290° C. (554° F.) and about 310° C. (590° F.). The term "green jet fuel" or "renewable jet fuel" means jet fuel comprising hydrocarbons not sourced from fossil fuels.

As used herein, the term "a component-rich stream" means that the rich stream coming out of a vessel has a greater concentration of the component than the feed to the vessel and preferably than all other streams withdrawn from the vessel.

As used herein, the term "a component-lean stream" means that the lean stream coming out of a vessel has a smaller concentration of the component than the feed to the vessel and preferably than all other streams withdrawn from the vessel.

DETAILED DESCRIPTION

The process and apparatus disclosed involves processing olefinic reactor product produced by the reaction of methanol over a catalyst to serve as feedstock for oligomerization utilizing a zeolitic catalyst. Zeolitic catalyst employed for the oligomerization of olefinic hydrocarbons is sensitive to a variety of contaminants, including CO, ethers, ketones, aldehydes, dienes, acetylenes, sulfur, and nitriles. These contaminants may cause permanent or temporary catalyst deactivation at ppm levels, so finding a suitable feedstock can be a challenge.

The olefinic product from the reaction of methanol over a catalyst is highly olefinic material and is an excellent feedstock for oligomerization utilizing a zeolitic catalyst. However, the olefinic product also contains a variety of contaminants which must be removed for the zeolitic catalyst to be effective. The olefinic reactor effluent can contain CO ranging from about 100 to about 1000 wppm, $CO_2$ ranging from about 50 to about 500 wppm, dimethyl ether (DME) ranging from about 1 to about 1.5 wt %, acetylenes ranging from about 20 to about 50 wppm, and dienes ranging from about 1000 to about 3000 wppm which must all be addressed prior to routing it to the oligomerization reactor. The olefinic reactor effluent can also contain unreacted methanol.

Figure 2:
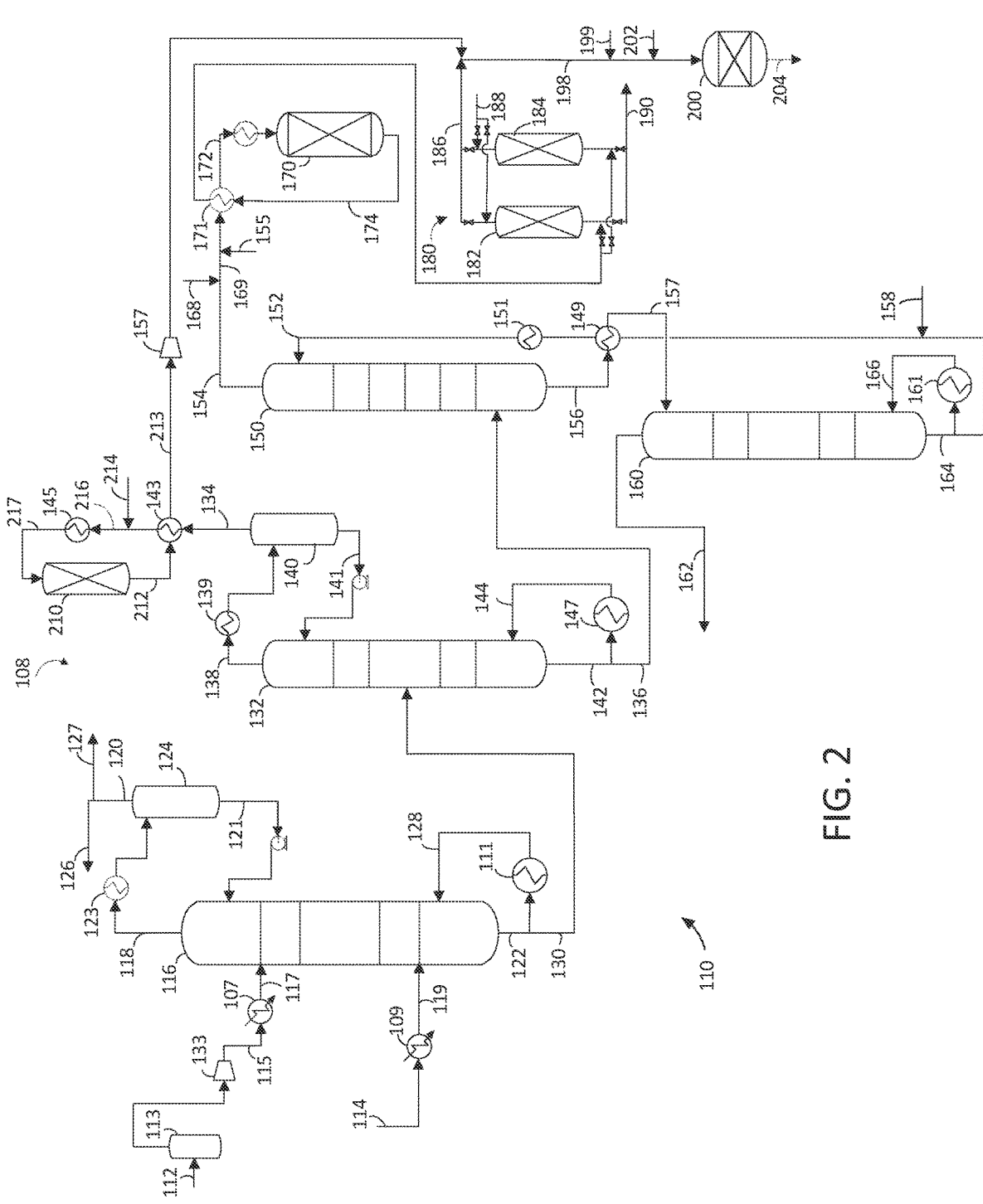
FIG. 2 is a schematic drawing of an oligomerization feed preparation process and apparatus of the present disclosure.

The process and apparatus may include an olefin recovery section 10 illustrated in FIG. 1 and an oligomerization feed preparation section 110 as illustrated in FIG. 2.

Turning to FIG. 1 of a process and apparatus 10, a superheated feed stream in line 12 is fed to an oxygenate conversion reactor 16 that reacts an oxygenate such as methanol or dimethyl ether (DME) with fluidized catalyst. A hot vaporous reactor effluent stream in line 14 is withdrawn from an oxygenate conversion reactor 16 which periodically or continuously circulates fluidized catalyst in a conventional manner to the regeneration zone 18 to maintain the selectivity and the conversion desired. Oxygenate conversion reactor 16 is maintained at effective conditions for the conversion of the oxygenate to produce light olefin products and generate oxygenated byproducts. The hot vaporous reactor effluent stream may comprise light olefins, water, and oxygenates. The oxygenate conversion reactor 16 may be operated to produce substantial or predominant propylene.

The hot vaporous reactor effluent stream in line 14 may be preliminarily cooled in a reactor effluent heat exchanger 15 to recover heat before it is passed to a quench tower 20. In the quench tower 20, the vaporous reactor effluent is desuperheated, neutralized of organic acids and clarified of catalyst fines by direct contact with a water stream supplied in line 19 which may be taken from a stripped water stream in line 21. A quenched reactor effluent stream in line 22 is discharged from the quench tower 20 and fed to a product separator column 24. The product separator column 24 may be in downstream communication with the oxygenate conversion reactor 16.

Product separator column 24 comprises two sections for separating the reactor effluent stream into a product olefin stream in an overhead line 40, an intermediate liquid stream in an intermediate line 28 and a product water stream in a bottoms line 26. A first, or lower, section receives the quenched reactor effluent stream in line 22. In the lower section, most of the heat is removed from the quenched reactor effluent stream while partially condensing the water in the quenched reactor effluent stream to generate a product water stream in bottoms line 26 comprising a portion of the oxygenate byproducts in the quenched reactor effluent stream in line 22. A portion of the product water stream is cooled and pumped around to the top of the first section of the product separator column 24 to cool the quenched reactor effluent stream in line 22. A second portion of the product water stream in bottoms line 26 is passed to a water stripper column 30. A water return stream comprising oxygenate byproducts from the compression section 80 in return line 32 can also be passed to the water stripper column 30. The water stripper column 30 may be in downstream communication with the product separator column 24.

A vapor stream from the first section of the product separator column 24 is passed to the second, or upper, section of the product separator. An intermediate stream in line 28 comprising hydrocarbons, oxygenate byproducts, and water in liquid phase is withdrawn at a bottom of the upper section. A portion of the intermediate stream in line 28 is cooled and passed as pump-around to the top of the second section of the product separator column 24. The remainder of the intermediate stream in line 28 is passed to a coalescer 29 to separate a hydrocarbon overhead stream from an aqueous stream in line 34 which is fed back to the product water stream and sent to the water stripper column 30 in line 36. An overhead product stream in line 40 comprising olefins from the product separator column 24 is delivered to the compression section 80.

The product water stream in line 36 includes dilute hydrocarbon oxygenates such as DME, methanol, acetaldehyde, acetone and methyl ethyl ketone (MEK). The water stripper column 30 separates or strips the oxygenates into a methanol and oxygenate rich stream in an overhead line 49 rich in both methanol and at least another oxygenate and a oxygenate-lean water stream in a bottoms line 46. A first portion of the oxygenate-lean water stream in line 46 is recycled to the process via a stripped water stream in line 21. A second portion is discharged in a waste-water stream in line 23.

In one embodiment the water stripper column 30 may operate at a temperature of about 115° C. (239° F.) to 200° C. (392° F.) at the bottom of the water stripper column and a pressure of about 70 kPa(g) (10 psig) to about 830 kPa(g) (120 psig) at the top of the water stripper column 30.

The product olefin stream in the product overhead line 40 carries valuable olefinic products which must be recovered. The compression section 80 increases the pressure of the product olefin stream necessary for downstream processing such as used in conventional light olefin recovery units. The compression section 80 may comprise a first knock out drum 82 which separates the product olefin stream into a pressurized first olefin rich stream at a temperature of about 20° C. (68° F.) to about 60° C. (140° F.) and a pressure of about 150 kPa(g) (22 psig) to about 280 kPa(g) (41 psig) in an overhead line 83 and a first aqueous stream rich in oxygenates in a bottoms line 84. The olefin rich stream in the overhead line 83 may be fed to a compressor 85, cooled and directed to a second knockout drum 86. The aqueous stream in the bottoms line 84 is pumped via a manifold line 76 to the return line 32 which returns the water stream with the product water stream in the product separator bottoms line 36 to the water stripper column 30.

The compression section 80 may comprise a second knock out drum 86 which separates the pressurized first olefin rich stream into a second pressurized olefin rich stream at a pressure of about 300 kPa(g) (44 psig) to about 400 kPa (g) (58 psig), and a temperature of about 20° C. (68° F.) to about 60° C. (140° F.) in an overhead line 87 and a second aqueous stream rich in oxygenates in a bottoms line 88. The second olefin rich stream in the overhead line 87 may be fed to a compressor 89, cooled and directed to a third knockout drum 90. The aqueous stream in the bottoms line 88 is pumped to the return line 32 via the manifold line 76 which returns the water stream with the product water stream in the product separator bottoms line 36 to the water stripper column 30.

The compression section 80 may comprise a third knock out drum 90 which separates the pressurized second olefin rich stream into a third pressurized olefin rich stream in an overhead line 91 and a third aqueous stream rich in oxygenates in a bottoms line 92. The third olefin rich stream in the overhead line 91 may be fed to the oxygenate absorber column 50. The aqueous stream in the bottoms line 92 is passed to the return line 32 via manifold line 76 which returns the water stream with the product water stream in the product separator bottoms line 36 to the water stripper column 30.

Types of suitable compressors may include centrifugal, positive displacement, piston, diaphragm, screw, and the like. In one embodiment, the compressors 85, 89 in the compression section 80 are centrifugal compressors. The final discharge pressure can be between about 1,0 MPa (g) (145 psig) and about 2.1 MPa (g) (305 psig). The compressor discharge may be cooled to about ambient temperatures using conventional heat transfer methods.

As illustrated in the FIG. 1 and according to a preferred embodiment, at least a portion of the compressed product stream via the overhead line 91 is contacted in the oxygenate absorber column 50 at effective conditions to absorb at least a quantity of effluent oxygenates with a cooled lean water stream in line 102 with no water taken directly from the product separator column 24 without prior removal of oxygenates. The contacting in the oxygenate absorber column 50 produces an absorption olefin rich stream in the overhead line 54 and an absorption water rich stream in a bottoms line 52 comprising a quantity of effluent oxygenates. The oxygenate absorber column 50 may have operating conditions including a bottoms temperature range of about 30° C. (86° F.) to about 60° C. (140° F.) and an overhead pressure range of about 700 kPa(g) (101 psig) to about 1 MPa(g) (145 psig).

The absorption olefin rich stream in the overhead line 54 may be fed to a third stage knock out drum 60 in which a gaseous olefin stream is taken in an overhead line 61 to a third compressor 62 while water and oxygenates are taken in the bottoms line 59 to the manifold line 76. The third stage knock out drum 60 may be operated at about the same pressure as the oxygenate absorber overhead and a temperature of about 32° C. (90° F.) to about 52° C. (125° F.). The gaseous olefin stream in line 61 is compressed in the third compressor 62 to form a compressed gaseous olefin stream in line 63, which is then combined with the stream in a stripper overhead line 71, partially condensed by cooling in a feed chiller 64 and fed in line 65 to a stripper separator 66. The stripper separator 66 separates an aqueous stream including oxygenates in the boot in line 67 which feeds the manifold line 76, a light olefinic vapor stream in an overhead line 68 comprising C3− olefins and a heavy olefinic liquid stream comprising C4+ olefins in line 69. The heavy olefinic liquid stream in line 69 is stripped in a DME stripper column 70 to remove C3− and lighter vapors in a stripper overhead line 71 from the heavy olefinic liquid stream in the stripper bottoms line 168. In an aspect, a reboil stream may be taken from the heavy olefinic liquid stream in the stripper bottoms line 168 which is reboiled in a DME stripper reboiler 167 and returned to the DME stripper column 70. Most oxygenates will be stripped into the stripper overhead line 71 and be separated after cooling upon recycle to the stripper separator 66. The bottom stream exiting the DME stripper column 70 may be sent through line 168 to the selective hydrogenation reactor 170 via line 169 as shown in FIG. 2. This stream comprises mostly C4+ olefins but comprises diolefins that will deter the oligomerization catalyst requiring selective hydrogenation. The DME stripper column 70 may be operated at an overhead temperature of about 60° C. (140° F.) to about 82° C. (180° F.) and a bottoms pressure of about 1.8 MPa (g) (260 psig) to about 2.2 MPa (g) (320 psig). The stripper separator 66 may operate at a temperature of about 10° C. (50° F.) to about 60° C. (140° F.) and a pressure of about 1.7 MPa(g) (250 psig) to about 2.1 MPa(g) (300 psig). The light olefinic vapor stream in the overhead line 68 is scrubbed in a caustic scrubber 73 by countercurrent contact with a caustic solution in line 42 to absorb acid gases such as carbon dioxide from the light olefinic vapor which exits the caustic scrubber 73 in an overhead line 74. The acid gas rich caustic solution exits caustic scrubber 73 in line 44. The caustic scrubber 73 may be operated at an overhead temperature of about 32° C. (90° F.) to about 54° C. (130° F.) and a pressure of about 1.7 MPa (g) (250 psig) to about 2.0 MPa (g) (290 psig).

The scrubbed light olefinic vapor stream in the overhead line 74 may be refrigerated by propylene refrigerant in a drier feed chiller 75 to liquefy part of the light olefinic vapor stream and provide a cooled scrubbed first vapor olefin stream in line 33. The cooled scrubbed first vapor olefin stream in line 33 is separated in a drier separator 45 to provide an aqueous stream from a boot in line 47 which is taken to the manifold line 76 and a vaporous light olefin stream comprising C3− hydrocarbons and gases in an overhead line 77 and a liquid light olefin stream in a bottoms line 78 comprising C3+ hydrocarbons. The vaporous light olefin stream in the overhead line 77 is dried in a drier 79a to provide a vaporous product olefin stream in line 112. The liquid light olefin stream in the bottoms line 78 is pumped to a drier 79b and dried to provide a liquid product olefin stream in line 114. The product olefin streams in lines 112 and 114 are processed in the oligomerization feed preparation section 110 in FIG. 2.

Turning to the oligomerization feed preparation section 110 of FIG. 2, a vaporous product olefin stream in line 112 is fed to a fractionation section 108. The vaporous product olefin stream in line 112 may comprise a C2− olefin stream and comprise predominantly ethylene. In an embodiment, a liquid product olefin stream in line 114 may be fed to the fractionation section 108. The liquid product olefin stream in line 114 may comprise a C3+ olefin stream and comprise predominantly propylene. The C3 olefin stream may also comprise C4-C8 olefins. In the fractionation section, the vaporous product olefin stream in line 112 and/or the liquid product olefin stream in line 114 are fractionated to provide a light gas stream in line 120 and a olefin rich stream in line 122.

In an embodiment, the vaporous product olefin stream in line 112 may be fed to a demethanizer fractionation column 116. The vaporous product olefin stream in line 112 may be fed to the top half of the demethanizer fractionation column 116. In an aspect, the vaporous product olefin stream in line 112 may be passed to a first suction drum 113 and then compressed in a first compressor 133. The vaporous product olefin stream may be taken in line 115 from the first compressor 133 and passed to a first heat exchanger 107. A cooled vaporous product olefin stream is taken in line 117 from the heat exchanger 107 and passed to the demethanizer fractionation column 116.

In an embodiment, a liquid product olefin stream in line 114 may be fed to the demethanizer fractionation column 116. The liquid product olefin stream in line 114 may be fed to the bottom half of the demethanizer fractionation column 116. In an aspect, the liquid product olefin stream in line 114 may be passed to a second heat exchanger 109. A cooled liquid product olefin stream is taken in line 119 from the heat exchanger 109 and passed to the demethanizer fractionation column 116. The vaporous product olefin stream and the liquid product olefin stream may be fractionated in the demethanizer fractionation column 116 together.

In an embodiment, the vaporous product olefin stream in line 115 and the liquid product olefin stream in line 114 may be combined and passed to a combined heat exchanger (not shown). A combined heat exchanged stream may be separated in the demethanizer fractionation column 116.

The vaporous product olefin stream and/or the liquid product olefin are fractionated preferably together in the demethanizer fractionation column 116 to provide an overhead light gas stream in an overhead light gas line 118 and a bottom olefin rich stream in a bottoms line 122 which may be considered a demethanized olefin rich stream. The overhead light gas stream in line 118 may comprise light gases of methane and lighter gases such as carbon monoxide, carbon dioxide, methane, nitrogen and hydrogen. Essentially all of the carbon monoxide will exit in the overhead light gas stream in line 118. The overhead light gas stream in line 118 is condensed in a demethanizer condenser 123 and fed to a demethanizer receiver 124. Condensed light gases are refluxed from the demethanizer receiver 124 to column 116 in a reflux line 121 while the light gas stream is taken in a net overhead line 120. A reactor purge gas stream in line 126 can be taken from the light gas stream to the oxygenate conversion reactor 16 and a fuel gas stream can be taken in line 127.

The olefin rich stream comprising C2+ olefins, typically C2-C8 olefins, in the demethanizer bottoms line 122 may be split into a reboil stream in line 128 which is reboiled in a demethanizer reboiler 111 and returned to the column and a net olefin rich stream in a net bottoms line 130. The demethanizer bottoms temperature may be about 0° C. (32° F.) to about 45° C. (113° F.) and a pressure of about 2.4 MPa (g) (350 psig) to about 3.5 MPa (g) (500 psig). Alternatively, the demethanizer bottoms temperature may be about −40° C. (−40° F.) to about 10° C. (50° F.) and the bottoms pressure may be about 0.7 MPa(g) (102 psig) to about 2.1 MPa(g) (305 psig).

The olefin rich stream comprises appreciable levels of dienes, acetylenes, dimethyl ether and other oxygenates which are all harmful to the oligomerization catalyst. In an embodiment, the olefin rich stream may be further fractionated to prepare the ethylene and the propylene separately. If ethylene is routed to the selective hydrogenation reactor 170, the ethylene may full saturate to ethane making it inert in an oligomerization reactor and unable to be oligomerized, negatively impacting jet fuel yield. Consequently, the net olefin rich stream in line 130 may be further fractionated in a deethanizer column 132.

The net olefin rich stream in line 130 is deethanized by fractionation in the deethanizer column 132 to provide an ethylene stream in a net overhead line 134 and a fractionated olefin rich stream in a deethanized net bottoms line 136. The fractionated olefin rich stream may be considered a deethanized olefin rich stream. The deethanizer column 132 may be operated at a bottoms temperature of about 43° C. (110° F.) to about 104° C. (220° F.) and an overhead pressure of about 1.8 MPa(g) (260 psig) to about 3.2 MPa(g) (460 psig).

An ethylene overhead stream in an overhead line 138 is condensed in a deethanizer condenser 139 and separated in a deethanizer receiver 140. Liquid from the deethanizer receiver 140 may be refluxed back to the deethanizer column 132 in the reflux line 141 from a bottom of the deethanizer receiver 140. A net overhead vapor stream from deethanizer receiver 140 in line 134 may be sent to an acetylene feed effluent exchanger 143 where it is heated by heat exchange with a concentrated ethylene stream in line 212 and combined with a hydrogen stream from line 214 to provide an acetylene converter feed stream in line 216. The acetylene converter feed stream in line 216 may be further heated in an acetylene converter feed heater 145 to provide a heated acetylene converter feed stream in line 217, which is charged to an acetylene conversion reactor 210. In the acetylene conversion reactor 210, acetylenes are converted to ethylene over an acetylene conversion catalyst in the presence of hydrogen thereby producing a concentrated ethylene stream in line 212. The concentrated ethylene stream in line 212 is cooled by heat exchange with the net overhead vapor stream in line 134 in acetylene feed effluent exchanger 143 to provide an ethylene stream in line 213. The deethanized stream in the bottoms line 142 may be split between a reboil stream in line 144 which is reboiled in a deethanizer reboiler 147 and returned boiling to the deethanizer column 132 to provide column heating requirements. The acetylene conversion catalyst may be a palladium and silver on aluminum oxide catalyst. The acetylene conversion conditions may include a pressure of about 1.4 MPa(g) (200 psig) to about 2.8 MPa(g) (400 psig) and a temperature of about 38° C. (100° F.) to about 93° C. (200° F.).

The fractionated olefin rich stream in the net bottoms line 136 may contain oxygenates such as dimethyl ether, methanol, and acetaldehydes in concentration that would poison selective hydrogenation catalyst and the oligomerization catalyst. Hence, the olefin rich stream in line 136 is routed to a water wash column 150 to absorb oxygenates such as dimethyl ether, methanol, and acetaldehydes from the fractionated olefin rich stream to provide an oxygenate rich water wash stream and a washed olefin rich stream. The washed olefin rich stream may be oligomerized.

In the water wash column 150, a water wash stream from a DME wash water stripper column 160 is routed in a cooled stripped wash water line 152 to a top third of the water wash column and counter-currently contacted with the fractionated olefin rich stream in the net bottoms line 136 fed to a bottom third of the water wash column. Countercurrent contact of the fractionated olefin rich stream and the water wash stream effects absorption of the oxygenates including DME from the fractionated olefin rich stream into the water wash stream. Absorption produces a washed olefin rich stream in an overhead line 154 and an oxygenate rich water wash stream in a bottoms line 156. The washed olefin rich stream in the overhead line 154 has a total oxygenate concentration of no more than 1000 wppm which is acceptable for the selective hydrogenation catalyst in the selective hydrogenation reactor 170. Suitably, the washed olefin rich stream in the overhead line 154 has a total oxygenate concentration of no more than 500 wppm to moderate the adsorbent bed sizes in the oxygenate removal unit 180. Preferably, the washed olefin rich stream in the overhead line 154 has a total oxygenate concentration of no more than 50 wppm. The water wash column 150 may be operated at a bottoms temperature of about 10° C. (50° F.) to about 66° C. (150° F.) and an overhead pressure of about 2.4 MPa (g) (350 psig) to about 3.2 MPa (g) (450 psig).

The oxygenate rich water wash stream in the bottoms line 156 is heated in a DME wash water exchanger 149 to produce a heated oxygenate rich water wash stream in line 157, which is fed to the DME wash water stripper column 160 to be stripped of DME and other oxygenates. In the DME wash water stripper column 160, DME and oxygenates are stripped from the oxygenate rich water wash stream to produce a recycle DME stream in line 162 which also contains other oxygenates which can be recycled to the oxygenate conversion reactor 16 in FIG. 1. A stripped water wash stream is produced in a bottoms line 164. A reboil stream in line 166 is taken from the stripped water wash stream in the bottoms line 164, reboiled in a DME wash water stripper reboiler 161 and transported back to the DME wash water stripper column 160. A cooled stripped wash water stream is taken from the stripped water wash stream in the bottoms line 164, cooled in a DME wash water exchanger 149 perhaps followed by a wash water cooler 151 to produce a cooled stripped wash water stream in line 152, and recycled to the water wash column 150 perhaps after supplementation with a make-up water stream in line 158. In an alternative embodiment, a make-up water stream in line 158 may be passed directly to the DME wash water stripper column 160.

The washed olefin rich stream in line 154 may be oligomerized in the oligomerization reactor 200 perhaps in liquid phase. However, the washed olefin rich stream in the water wash overhead line 154 comprising C3 to C8 olefins also contains diolefins that could cause cross-link polymerization in the oligomerization reactor. Therefore, it may be selectively hydrogenated to convert diolefins and acetylenes to mono-olefins before passing it to the oligomerization reactor. The C4+ olefins in the DME stripped line 168 from FIG. 1 may also contain diolefins and can accordingly also benefit from selective hydrogenation prior to oligomerization. The washed olefin rich stream in the water wash overhead line 154 may be combined with the heavy olefin stream in line 168 to provide a combined olefin stream in a combine line 169. The combined olefin stream in the combine line 169 may be mixed with hydrogen from line 155 heated perhaps by heat exchange in a heat exchanger 171 with the mono-olefin stream in line 174 and charged to the selective hydrogenation reactor 170 in the selective hydrogenation reactor charge line 172. In the selective hydrogenation reactor 170, diolefins and residual acetylenes are converted to mono-olefins to provide the mono-olefin stream in line 174. Selective hydrogenation effects just minimal hydrogenation of mono-olefins to paraffins.

The selective hydrogenation reactor 170 is normally operated at relatively mild hydrogenation conditions. These conditions will normally result in the hydrocarbons being present as liquid phase materials. The reactants will normally be maintained under the minimum pressure sufficient to maintain the reactants as liquid phase hydrocarbons. Suitable operating pressures include about 2.3 MPa(g) (330 psig) to about 3.1 MPa(g) (450 psig). A relatively moderate temperature between about 20° C. (68° F.) and about 100° C. (212° F.) is typically employed. The liquid hourly space velocity of the reactants through the selective hydrogenation catalyst should be above about 1.0 hr$^{-1}$ and below about 35.0 hr$^{-1}$. To avoid the undesired saturation of a significant amount of mono-olefinic hydrocarbons, the mole ratio of hydrogen to diolefinic hydrocarbons in the selective hydrogenation reactor charge line 17 2 entering the bed of selective hydrogenation catalyst is maintained between 1:1 and 4.5:1.

Suitable selective hydrogenation catalysts include, but are not limited to, a catalyst comprising copper and at least one other metal such as titanium, vanadium, chrome, manganese, cobalt, nickel, zinc, molybdenum, palladium, and cadmium or mixtures thereof. The metals are preferably supported on inorganic oxide supports such as silica and alumina, for example. The mono-olefin stream may exit the reactor in line 174 with a greater concentration of mono-olefins and a smaller concentration of acetylenes and dienes than in the selective hydrogenation reactor charge stream in line 172. The mono-olefin stream in line 174 may comprise an acetylene and diolefin concentration of no more than about 50 to about 80 wppm.

The mono-olefin stream in line 174 may be oligomerized in the oligomerization reactor 200 perhaps in mixed or liquid phase. However, the mono-olefin stream still has a large concentration of oxygenates that could suppress the oligomerization catalyst activity. Accordingly, the selectively hydrogenated stream in line 174 may be transported to an oxygenate removal unit 180 to adsorb residual oxygenates including DME, water, and other trace oxygenates. The oxygenate removal unit 180 may comprise one or more adsorbent vessels 182, 184, so one or more adsorbent vessel(s) 182 or 184 can be charged with the mono-olefin stream in line 174 by appropriate valve control to adsorb oxygenates therefrom and one of the other adsorbent vessel 184 or 182 can be fed with a regenerant stream from line 188 by appropriate valve control and undergoing regeneration. The mono-olefin stream in line 174 may flow upwardly in the adsorbent vessel(s) 182, 184, but downward flow is also suitable. Three adsorbent vessels may be used in the oxygenate removal unit. A deoxygenated olefin stream can be recovered from the oxygenate removal unit 180 in line 186. An oxygenated regenerant stream may be recovered from the oxygenate removal unit 180 in line 190. The deoxygenated olefin stream in line 186 comprises C3 to C8 olefins and not more than 1 wppm oxygenate including DME and water.

When an adsorbent vessel 182, 184 requires regeneration, it can be taken off-stream with the selectively hydrogenated stream in line 174 and contacted with a heated vaporous regenerant from line 188 through appropriate valve control in a direction counter to the normal flow of the olefinic selectively hydrogenated stream. The regenerant may be a clean inert gas such as nitrogen, hydrogen, natural gas and light paraffins such as propane, butanes and pentanes. The regenerant can fully restore the capacity of the adsorbent in the regenerated vessel 182, 184. The spent regenerant can leave the oxygenate removal unit 180 in a spent regenerant line 190. The oxygenate removal unit may be operated at an inlet temperature of about 10° C. (50° F.) to about 66° C. (150° F.) and an inlet pressure of about 2.3 MPa (gauge) (330 psig) to about 3 MPa (gauge) (430 psig). The adsorbent in the oxygenate removal unit 180 may be a large pore molecular sieve such as 13X.

The deoxygenated olefin stream in line 186 may provide an oligomerization charge stream in line 198 that can be charged to an oligomerization reactor 200. Alternatively or cumulatively, the concentrated ethylene stream in line 213 may be compressed in a compressor 157 to a higher pressure and charged to one or more oligomerization reactors 200 in the oligomerization charge stream in line 198. The oligomerization reactor 200 may comprise a two-stage reactor system and each stage may comprise multiple beds.

The oligomerization charge stream in line 198 may be contacted with an oligomerization catalyst in an oligomerization reactor 200 to oligomerize the ethylene, propylene, and C4+ olefins to oligomers. A third stream comprising unreacted C3+ olefin in a recycle line 199 may be passed to the oligomerization reactor 200. In an embodiment, the third stream in line 199 may be combined with the oligomerization charge stream in line 198 and passed to the oligomerization reactor 200. The oligomerization reaction generates a large exotherm. Consequently, this large exotherm must be managed. To manage the exotherm, the charge olefin stream may be diluted with a diluent stream in line 202 to provide a diluted olefin stream to absorb the exotherm. The diluent stream may comprise a paraffin stream. Additionally, the charge olefin stream may be split and charged to a plurality of oligomerization reactors 200. The oligomerization reaction temperature may be about 110° C. (230° F.) to about 260° C. (500° F.) and the oligomerization pressure may be about 3.5 MPag (500 psig) to about 8.4 MPa (1200 psig). The charge olefin stream in line 198 may be cooled prior to charging the oligomerization reactor 200. An oligomerized stream may be discharged from the oligomerization reactor 200 in line 204.

Figure 3:
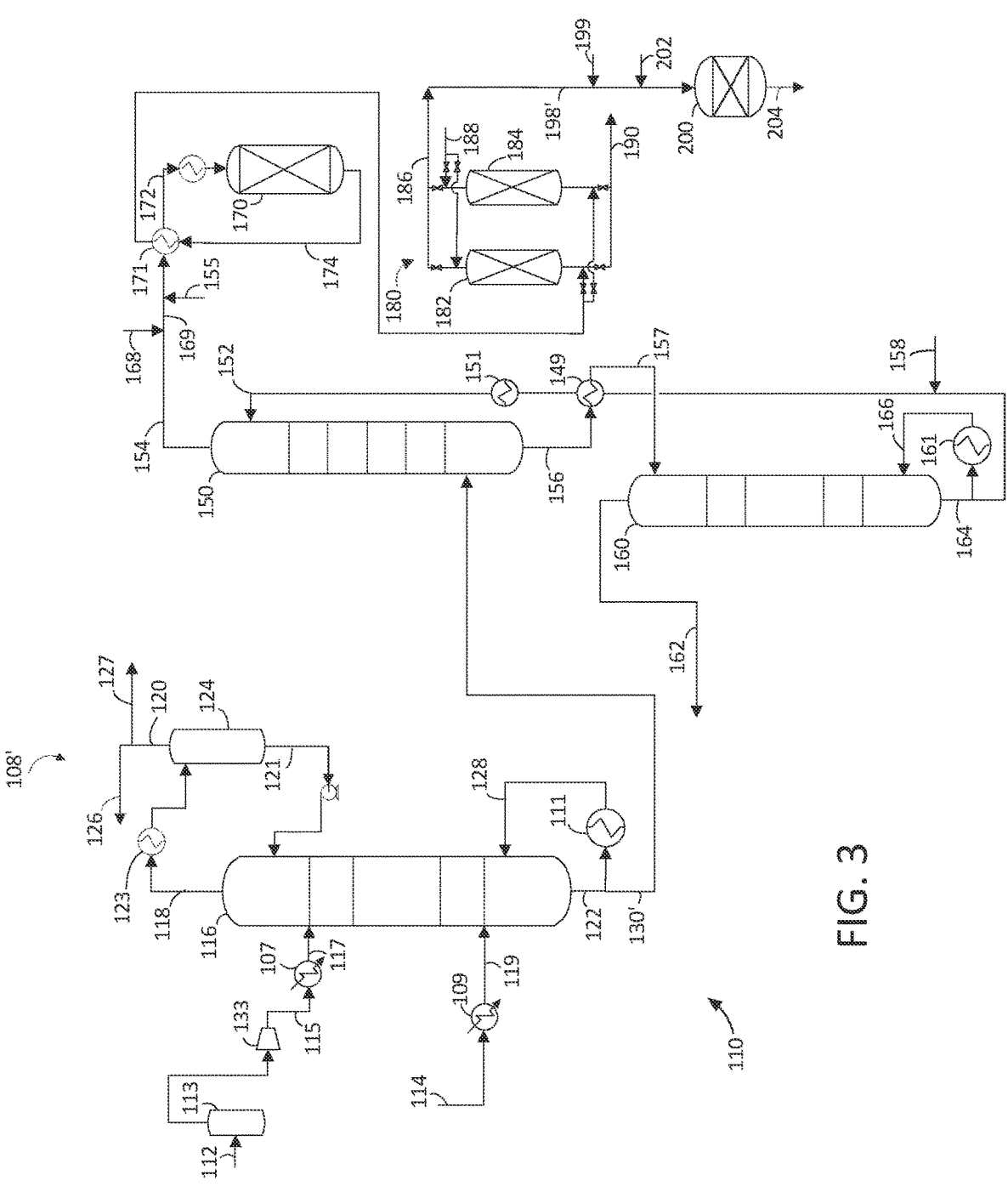
FIG. 3 is a schematic drawing of an alternative embodiment of the oligomerization feed preparation process and apparatus of the present disclosure.

FIG. 3 depicts an embodiment that omits a deethanizer column and the acetylene converter. Many of the elements in FIG. 3 have the same configuration as in FIG. 2 and bear the same reference number. Elements in FIG. 3 that correspond to elements in FIG. 2 but have a different configuration bear the same reference numeral as in FIG. 2 but are marked with a prime symbol (').

In the embodiment of FIG. 3, the fractionation section 108' only comprises a demethanizer fractionation column 116. The olefin rich stream in a demethanizer net bottoms line 130' is transported directly to the water wash column 150. The water wash column 150 absorbs oxygenates from the olefin rich stream into a cooled stripped wash water stream in line 152 to provide an oxygenate rich water wash stream in line 156 and a washed olefin stream in line 154 which may be selectively hydrogenated in the selective hydrogenation reactor 170 and/or subjected to oxygenate removal in the oxygenate removal unit 180 to provide the charge stream in line 198' to the oligomerization reactor 200. With the foregoing exceptions, FIG. 3 is configured and operates as the embodiment depicted in FIG. 2.

Figure 4:
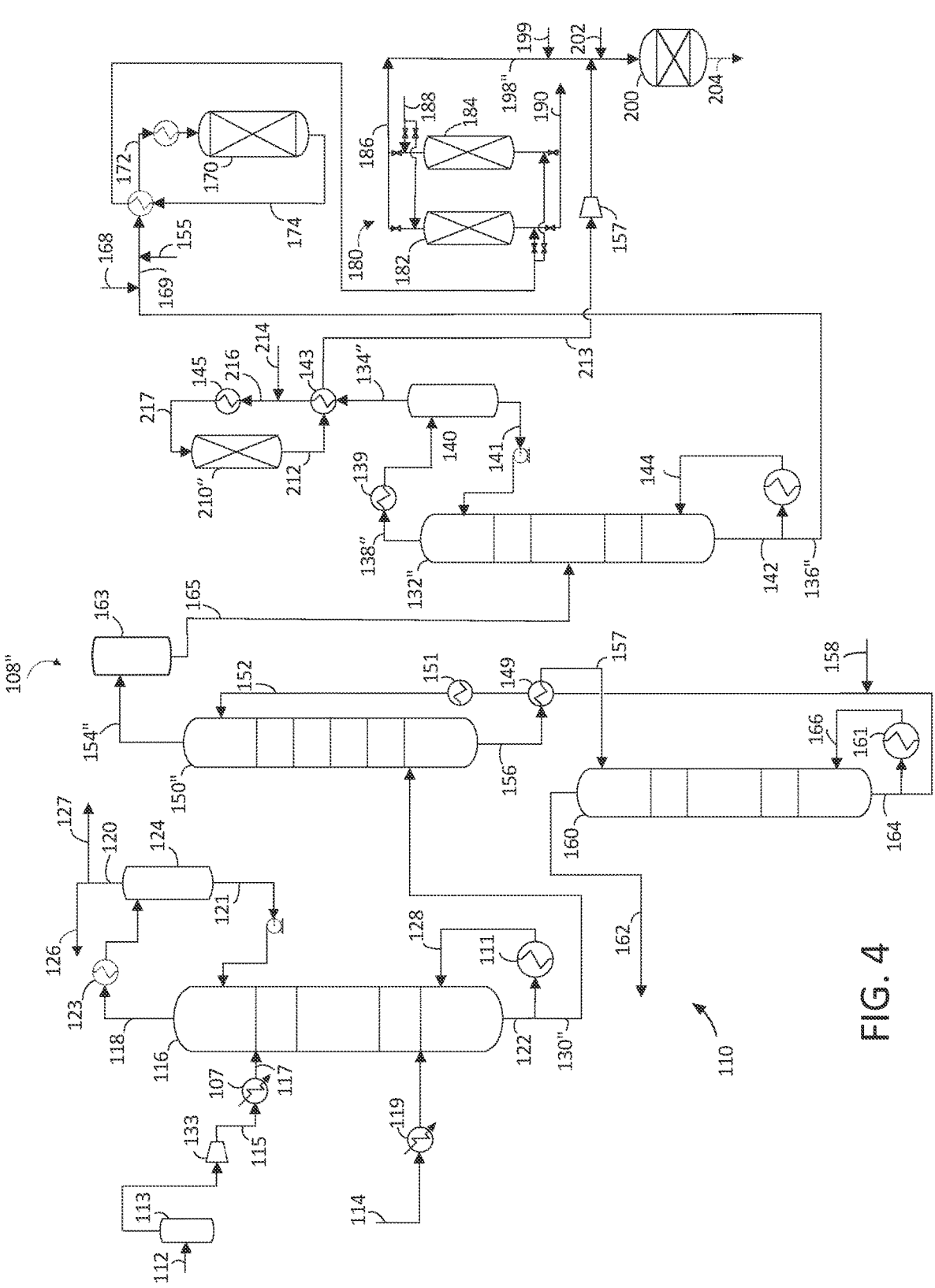
FIG. 4 is a schematic drawing of a further alternative embodiment of the oligomerization feed preparation process and apparatus of the present disclosure.

FIG. 4 depicts an embodiment that moves the deethanizer column 132" and the acetylene converter downstream of the water wash column 150". Many of the elements in FIG. 4 have the same configuration as in FIG. 2 and bear the same reference number. Elements in FIG. 4 that correspond to elements in FIG. 2 but have a different configuration bear the same reference numeral as in FIG. 2 but are marked with a double prime symbol (").

In the embodiment of FIG. 4, in the fractionation section 108", the olefin rich stream in a demethanizer net bottoms line 130" is transported directly to the water wash column 150". The water wash column 150" absorbs oxygenates from the olefin rich stream into a cooled stripped wash water stream in line 152 to provide an oxygenate rich water wash stream in line 156 and a washed olefin stream in line 154". The washed olefin stream in line 154" is dried in a drier 163 to provide a dried washed olefin stream in line 165. The dried washed olefin stream in line 165 is then deethanized in the deethanizer fractionation column 132" to provide a fractionated olefin rich stream in the deethanizer net bottoms line 136" and an ethylene stream in a deethanizer overhead line 138". The fractionated olefin rich stream in the deethanizer net bottoms line 136" may be selectively hydrogenated in the selective hydrogenation reactor 170 and/or subjected to oxygenate removal in the oxygenate removal unit 180 to provide the charge stream in line 198" to the oligomerization reactor 200. The ethylene stream in the deethanizer overhead line 138" may be subjected to acetylene conversion in the acetylene conversion reactor 210" to produce a concentrated ethylene stream in line 134". The concentrated ethylene stream can be combined with the mono-olefin stream in line 174 or the deoxygenated olefin stream in line 186 to provide the oligomerization charge stream in line 198" and oligomerized in the oligomerization reactor 200. With the foregoing exceptions, FIG. 4 is configured and operates as the embodiment depicted in FIG. 2.

EXAMPLE

We simulated operation of the acetylene conversion reactor. Over 150 mol ppm of acetylene was in the acetylene converter feed stream to the acetylene conversion reactor. Hydrogen was added to the acetylene converter feed stream and it was heated. After hydrogenation in the reactor, less than 50 mol ppm of acetylene was in the acetylene converter product.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for processing an olefin stream comprising fractionating an olefin stream to provide a light gas stream and an olefin rich stream; selectively hydrogenating the olefin rich stream to convert diolefins to mono-olefins and provide a mono-olefin stream; and oligomerizing the mono-olefin stream over an oligomerization catalyst to provide an oligomerized stream. An embodiment of the disclosure is one, any or all of prior embodiments in this paragraph up through the first embodiment in this paragraph further comprising absorbing oxygenates from the olefin rich stream into a water wash stream to provide an oxygenate rich water wash stream and a washed olefin rich stream and the olefin rich stream that is selectively hydrogenated is the washed olefin rich stream. An embodiment of the disclosure is one, any or all of prior embodiments in this paragraph up through the first embodiment in this paragraph wherein the fractionating step comprises demethanizing the olefin stream to provide the light gas stream and the olefin rich stream. An embodiment of the disclosure is one, any or all of prior embodiments in this paragraph up through the first embodiment in this paragraph further comprising fractionating the olefin rich stream to provide a fractionated olefin rich stream and an ethylene stream. An embodiment of the disclosure is one, any or all of prior embodiments in this paragraph up through the first embodiment in this paragraph further comprising absorbing oxygenates from the fractionated olefin rich stream into a water wash stream to provide an oxygenate rich water wash stream and a washed olefin rich stream and the olefin rich stream that is selectively hydrogenated is the washed olefin rich stream. An embodiment of the disclosure is one, any or all of prior embodiments in this paragraph up through the first embodiment in this paragraph further comprising absorbing oxygenates from the fractionated olefin rich stream into a water wash stream to provide an oxygenate rich water wash stream and a washed olefin rich stream, and the olefin rich stream that is selectively hydrogenated is the washed olefin rich stream. An embodiment of the disclosure is one, any or all of prior embodiments in this paragraph up through the first embodiment in this paragraph further comprising absorbing oxygenates from the mono-olefin stream before oligomerizing the mono-olefin stream. An embodiment of the disclosure is one, any or all of prior embodiments in this paragraph up through the first embodiment in this paragraph further comprising converting acetylenes in the ethylene stream to ethylene in the presence of hydrogen to provide a concentrated ethylene stream. An embodiment of the disclosure is one, any or all of prior embodiments in this paragraph up through the first embodiment in this paragraph further comprising oligomerizing the concentrated ethylene stream. An embodiment of the disclosure is one, any or all of prior embodiments in this paragraph up through the first embodiment in this paragraph further comprising oligomerizing the concentrated ethylene stream and the mono-olefin stream together. An embodiment of the disclosure is one, any or all of prior embodiments in this paragraph up through the first embodiment in this paragraph further comprising compressing a product olefin stream to provide a compressed product olefin stream; stripping the compressed product olefin stream to provide a light olefin stream and a heavy olefin stream; and selectively hydrogenating the heavy olefin stream with the olefin rich stream to convert diolefins to mono-olefins to provide the mono-olefin stream. An embodiment of the disclosure is one, any or all of prior embodiments in this paragraph up through the first embodiment in this paragraph, wherein the olefin rich stream is a demethanized olefin rich stream. An embodiment of the disclosure is one, any or all of prior embodiments in this paragraph up through the first embodiment in this paragraph wherein the olefin stream is taken from an oxygenate conversion reactor. An embodiment of the disclosure is one, any or all of prior embodiments in this paragraph up through the first embodiment in this paragraph, wherein the oxygenates absorbed from the olefin rich stream comprise one or more of dimethyl ether, methanol, and acetaldehyde. An embodiment of the disclosure is one, any or all of prior embodiments in this paragraph up through the first embodiment in this paragraph wherein the olefin rich stream is a demethanized olefin rich stream comprising C2 to C8 olefins. An embodiment of the disclosure is one, any or all of prior embodiments in this paragraph up through the first embodiment in this paragraph wherein the olefin rich stream comprises C3 to C8 olefins. An embodiment of the disclosure is one, any or all of prior embodiments in this paragraph up through the first embodiment in this paragraph wherein the lighter gas stream includes carbon monoxide, carbon dioxide, nitrogen, hydrogen, and methane.

A second embodiment of the disclosure is a process for processing an olefin stream comprising fractionating an olefin stream to provide a light gas stream and an olefin rich stream; absorbing oxygenates from the olefin rich stream into a water wash stream to provide an oxygenate rich water wash stream and a washed olefin rich stream; selectively hydrogenating the washed olefin rich stream to convert diolefins to mono-olefins and provide a mono-olefin stream; and oligomerizing the mono-olefin stream over an oligomerization catalyst to provide an oligomerized stream. An embodiment of the disclosure is one, any or all of prior embodiments in this paragraph up through the second embodiment in this paragraph further comprising compressing a product olefin stream to provide a compressed product olefin stream; stripping the compressed product olefin stream to provide a light olefin stream and a heavy olefin stream; and selectively hydrogenating the heavy olefin stream with the washed demethanized olefin rich stream to convert diolefins to mono-olefins to provide the mono-olefin stream.

A third embodiment of the disclosure is a process for processing an olefin stream comprising fractionating a vaporous olefin stream and a liquid olefin stream to provide a light gas stream and an olefin rich stream; selectively hydrogenating the olefin rich stream to convert diolefins to mono-olefins and provide a mono-olefin stream; and oligomerizing the mono-olefin stream over an oligomerization catalyst to provide an oligomerized stream.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for processing an olefin stream comprising:
converting methanol to provide an olefin stream;
fractionating said olefin stream to provide a gas stream and an olefin rich stream;
selectively hydrogenating said olefin rich stream to convert diolefins to mono-olefins and provide a mono-olefin stream; and
oligomerizing said mono-olefin stream over an oligomerization catalyst to provide an oligomerized stream.

2. The process of claim 1 further comprising absorbing oxygenates from said olefin rich stream into a water wash stream to provide an oxygenate rich water wash stream and a washed olefin rich stream and the olefin rich stream that is selectively hydrogenated is said washed olefin rich stream.

3. The process of claim 2, wherein the oxygenates absorbed from said olefin rich stream comprise one or more of dimethyl ether, methanol, and acetaldehyde.

4. The process of claim 1 wherein said fractionating step comprises demethanizing said olefin stream to provide said light gas stream and said olefin rich stream.

5. The process of claim 4 further comprising fractionating said olefin rich stream to provide a fractionated olefin rich stream and an ethylene stream and the olefin rich stream that is selectively hydrogenated is said fractionated olefin rich stream.

6. The process of claim 5 further comprising absorbing oxygenates from said fractionated olefin rich stream into a water wash stream to provide an oxygenate rich water wash stream and a washed olefin rich stream and the olefin rich stream that is selectively hydrogenated is said washed olefin rich stream.

7. The process of claim 5 further comprising converting acetylenes in said ethylene stream to ethylene in the presence of hydrogen to provide a concentrated ethylene stream.

8. The process of claim 7 further comprising oligomerizing said concentrated ethylene stream.

9. The process of claim 8 further comprising oligomerizing said concentrated ethylene stream and said mono-olefin stream together.

10. The process of claim 5 wherein said olefin rich stream comprises C3 to C8 olefins.

11. The process of claim 4 further comprising absorbing oxygenates from a fractionated olefin rich stream into a water wash stream to provide an oxygenate rich water wash stream and a washed olefin rich stream, and the olefin rich stream that is selectively hydrogenated is said washed olefin rich stream.

12. The process of claim 1 further comprising absorbing oxygenates from said mono-olefin stream before oligomerizing said mono-olefin stream.

13. The process of claim 1 further comprising compressing a product olefin stream produced from the methanol to provide a compressed product olefin stream; stripping said compressed product olefin stream to provide a light olefin stream and a heavy olefin stream; and selectively hydrogenating said heavy olefin stream with said olefin rich stream to convert diolefins to mono-olefins to provide said mono-olefin stream.

14. The process of claim 13, wherein the olefin rich stream is a demethanized olefin rich stream.

15. The process of claim 1 wherein the olefin stream is taken from an oxygenate conversion reactor.

16. The process of claim 1 wherein said olefin rich stream is a demethanized olefin rich stream comprising C2 to C8 olefins.

17. The process of claim 1 wherein said lighter gas stream includes carbon monoxide, carbon dioxide, nitrogen, hydrogen, and methane.

18. A process for processing an olefin stream comprising:
converting methanol to provide an olefin stream;
fractionating said olefin stream to provide a gas stream and an olefin rich stream;
absorbing oxygenates from said olefin rich stream into a water wash stream to provide an oxygenate rich water wash stream and a washed olefin rich stream;
selectively hydrogenating said washed olefin rich stream to convert diolefins to mono-olefins and provide a mono-olefin stream; and
oligomerizing said mono-olefin stream over an oligomerization catalyst to provide an oligomerized stream.

19. The process of claim 18 further comprising compressing a product olefin stream produced from methanol to provide a compressed product olefin stream; stripping said compressed product olefin stream to provide a light olefin stream and a heavy olefin stream; and selectively hydrogenating said heavy olefin stream with said washed demethanized olefin rich stream to convert diolefins to mono-olefins to provide said mono-olefin stream.

20. A process for processing an olefin stream comprising:
sending a vaporous olefin stream and a liquid olefin stream to a fractionation column;
fractionating said vaporous olefin stream and said liquid olefin stream to provide a gas stream and an olefin rich stream;
selectively hydrogenating said olefin rich stream to convert diolefins to mono-olefins and provide a mono-olefin stream; and
oligomerizing said mono-olefin stream over an oligomerization catalyst to provide an oligomerized stream.

* * * * *